May 16, 1972 W. H. DANIEL Plant Pat. 3,176
KENTUCKY BLUEGRASS (POA PRATENSIS)
Filed July 7, 1969
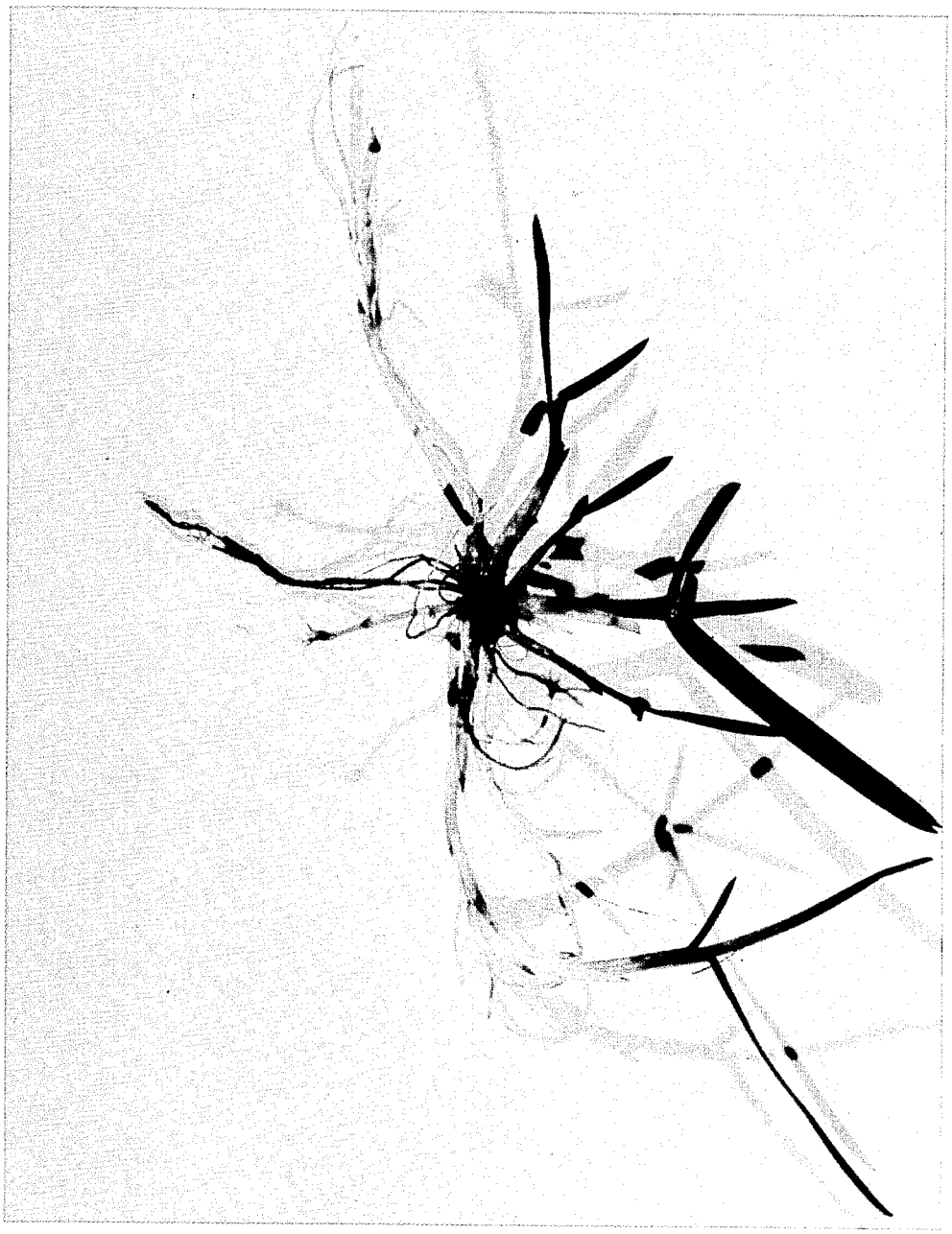
INVENTOR.
WILLIAM H. DANIEL
BY: J. Merbitt
ATTORNEY.

United States Patent Office

Plant Pat. 3,176
Patented May 16, 1972

3,176

KENTUCKY BLUEGRASS (*POA PRATENSIS*)

William H. Daniel, West Lafayette, Ind., assignor to Purdue Research Foundation

Filed July 7, 1969, Ser. No. 839,733
Int. Cl. A01h *5/00*
U.S. Cl. Plt.—88 1 Claim

This invention relates to a new and distinctive Kentucky blue-grass, *Poa pratensis,* designated as RI–10. Its faster spread and improved seed production, compared to Anheuser Dwarf, indicated desired improvements.

As history it was selected as best of many seedlings (planted individually in pots in greenhouse and transplanted in spring 1962). Seed came one plant within one (1) acre of spaced seedlings of Anheuser Dwarf parentage as individually field grown and harvested by Jacklin Seed Company, Dishman, Wash., per letter dated Jan. 18, 1962.

Its powdery mildew (*Erysiphe graminis*) resistance is excellent. Leafspot (*Helminthosporium vagans*) resistance rated 3 (1 best—9 range) and in later ratings 1966 rating was 1 (free). Its stem rust rating, 6 was below average (1 best—9 worst) field 9 AI, fall 1967.

In greenhouse rows, 1963, its low growth and early tillering was noted as best of 117 selections in the series. Shade tolerance is indicated by fast development in greenhouse during low light period during winter.

Pot Cultures From Seedlings, Spring, 1967

| Selection | Early Tillers rhizomes | Later rhizomes | Source |
|---|---|---|---|
| Line D, RI–10 | 16–2 | 33 | Page 45, Book 22, Purdue. |
| Windsor (standard) | 12–1 | 20 | |

ing of 3 (1–9 range). Actual yields when in test of 3630 spaced plants from over 100 seed sources in 1968 for a 4 row test in breeder's fields was 118 pounds, where Anheuser Dwarf produced 84 pounds. The seedheads averaged 15 inches height at Lafayette, in 1967. In eastern Washington where Windsor may excess 30 inches and common types exceed 36 inches RI–10 was only 26″ in first year seed fields. In 1970 the same field has older sod and different year and seed head averaged 22 inches. The seed is darker (more brown than Merion) and develops in sturdy, wide well developed spikelets and panicles. Its medium late maturity, greeness of leaves, good seed yield and leafspot resistance add to and exceed its parentage.

At normal nutrition the single emerging tiller from each rhizome distinguishes RI–10 from Windsor, Fylking or Merion since these tend to put up multi-tillers from each terminal. Thus more open space turf is characteristic of RI–10 (example where Merion had 26 leaves per square inch RI–10 had only 15 under 2″ moved turf conditions in 1967). However, at high nitrogen, where growth is forced, the excellent disease resistance favors dense turf due to longevity of leaves (much desired).

Thus RI–10 with increased seed production improved leafspot resistance is an addition to the cultivars of bluegrass elsewhere described in co-pending U.S. plant patent application Nos. 839,731, 839,732 and 839,733.

Comparison of RI–10, with AQ6, Dwarf and 16–BB–56 are as follows:

| | Dwarf | AQ6 | 16–BB–56 | RI–10 |
|---|---|---|---|---|
| Plants, number of | 285 | 39 | 35 | 200 |
| Years when data was taken | 1965–68 | 1966 | 1966–68 | 1965–68 |

| Character | Dwarf | AQ6 | 16–BB–56 | RI–10 | Comment |
|---|---|---|---|---|---|
| Leaf height, inches | 7.2 | 5.2 | 8.5 | 6.6 | Low. |
| Spread rating, 1 most | 5.9 | 5.1 | 4.7 | 5.8 | Only medium. |
| Color-rating, 1 greenest | 3.3 | 1.3 | 3.7 | 3.2 | Dark green. |
| Stripe smut resistance 1 best | 1 | 1 | 1 | 1 | None observed anywhere. |
| Maturing of seedtime rating, 1 earliest | 5.4 | 4.5 | 5.5 | 4.8 | Medium late. |
| Qualtiy of seed rating 1 most | 5.7 | 4.2 | 3.8 | 4.4 | About average. |
| Seedhead height, inches | 14.2 | 14.5 | 19.3 | 15.2 | In lower 50%. |

NOTE.—Ratings range: 1 most desired; 3 is good; 5 is average; 9 least desired.

Its low growing characteristics are confirmed via height of regrowth after mowing. When within all entries length ranged from 6 to 24 cm. RI–10 had only 8 cm. regrowth.

Besides being short the leaf is wide, dark green, and remains green for long periods both in turf and in seed fields. Such distinguishes RI–10 from common types, which matures leaves earlier. As a way of identity, Merion and Windsor sheaths remain green but RI–10 sheaths show purpling at ample nutrition and high temperatures. Clipping of RI–10 may also show purpling character as they slow dry.

Improved seed production is indicated by a good rat-

Many distinctive characteristics of RI–10 as respects most other bluegrasses are similar to Dwarf, and except when noted otherwise in the foregoing table, it may be assumed that the distinctions of Dwarf as respects other bluegrasses are similar for RI–10.

I claim:

1. A new and distinct variety of bluegrass plant, substantially as described and illustrated.

No references cited.

ROBERT E. BAGWILL, Primary Examiner